(12) United States Patent
Dyer

(10) Patent No.: US 6,525,071 B2
(45) Date of Patent: Feb. 25, 2003

(54) COMPOSITIONS AND METHODS FOR THE TREATMENT AND PREVENTION OF BOVINE MASTITIS

(75) Inventor: David L. Dyer, Cypress, CA (US)

(73) Assignee: MCJ, Inc., Seal Beach, CA (US)

( * ) Notice: Subject to any disclaimer, the term of this patent is extended or adjusted under 35 U.S.C. 154(b) by 0 days.

(21) Appl. No.: 09/812,268

(22) Filed: Mar. 20, 2001

(65) Prior Publication Data

US 2002/0165260 A1 Nov. 7, 2002

Related U.S. Application Data

(60) Provisional application No. 60/272,947, filed on Mar. 2, 2001.

(51) Int. Cl.$^7$ .............................................. A61K 31/415
(52) U.S. Cl. ........................................ 514/320; 514/643
(58) Field of Search .................................. 514/390, 643

(56) References Cited

U.S. PATENT DOCUMENTS

| | | | |
|---|---|---|---|
| 3,250,681 A | 5/1966 | Zbornik et al. ............... | 167/85 |
| 3,251,824 A | 5/1966 | Battista ....................... | 260/230 |
| 3,347,743 A | 10/1967 | Reuter et al. .............. | 167/53.2 |
| 3,639,623 A | 2/1972 | Ritschel et al. ............. | 424/311 |
| 3,830,920 A | 8/1974 | McKenzie et al. .......... | 425/258 |
| 3,993,777 A | 11/1976 | Caughman et al. ......... | 424/329 |
| 4,766,113 A | * 8/1988 | West et al. ................. | 514/187 |
| 5,661,170 A | 8/1997 | Chodosh .................... | 514/390 |
| 5,827,870 A | * 10/1998 | Chodosh .................... | 514/390 |
| 6,087,400 A | * 7/2000 | Dyer et al. .................. | 514/643 |

FOREIGN PATENT DOCUMENTS

| | | |
|---|---|---|
| GB | 1 554 615 | 10/1979 |
| GB | 2 182 245 A | 5/1987 |
| WO | WO 99/25190 | 5/1999 |
| WO | WO 00/521126 | 9/2000 |

OTHER PUBLICATIONS

Dyer, D.L. et al., "Testing a new alcohol–free hand sanitizer to combat infection", *AORN Journal,* 1998, 68(2), 239–251 (missing pages were advertisements).

Dyer, D.L., Ph.D. Handwashing: Problems and solutions: Part 1, *Infection Control Today,* Apr. 2000.

Moak (1916,2).

Funk et al., "Propylene Glycol Dermatitis: re–evaluation of an old problem", *Contact Dermatitis,* 1993, 31, pp. 236–241.

Trancik et al., "Propylene glycol: Irritation of sensitization?", *Contact Dermatitis,* 1982, 8, pp. 185–189.

Botelho, "The minimum inhibitory concentration of oral antibacterial agents against cariogenic organisms", *Microbios,* 2000, 103, pp. 31–41.

* cited by examiner

Primary Examiner—James H. Reamer
(74) *Attorney, Agent, or Firm*—Woodcock Washburn LLP

(57) ABSTRACT

An antimicrobial composition containing between about 0.0005 and about 1 weight percent of an antimicrobial agent; between about 0.05 and about 5 weight percent of a keratolytic agent; between about 0.001 and about 10 weight percent of a surfactant; and at least about 60 weight percent water.

30 Claims, No Drawings

COMPOSITIONS AND METHODS FOR THE TREATMENT AND PREVENTION OF BOVINE MASTITIS

This application claims the benefit of Ser. No. 60/272,941 filed Mar. 3, 19998.

FIELD OF THE INVENTION

The present invention is directed to antimicrobial compositions and methods of using the same. More specifically, this invention relates to water-based, antimicrobial compositions and methods of using the same for the treatment and prevention of bovine mastitis.

BACKGROUND OF THE INVENTION

It has been the trend of the dairy industry over the last few decades to increase milking frequency (i.e. cow milkings per day) with the goal of either 1) increasing net milk production or 2) maintaining existing production levels with fewer animals. For example, in the early part of the last century, the great majority of dairies milked cows once or twice daily. Presently, improvements in dairy management, along with improvements in dairy stock and animal nutrition have allowed about 30% of dairies to maintain a three-times daily milking schedule. It is very likely that within the next two decades, four-times daily milking will be commonplace due to further improvements to livestock and increased process automation.

Milking is routinely done with semi-automated milking machines in developed countries. However, frequent exposure to this process is traumatic to udder and teat tissue, due to the milking mechanism's alternation of pressure and vacuum on wet skin. Such trauma can impair the integrity of the protective layers of the skin, and result in chapping, peeling and irritation. Such roughened unhealthy skin surface has been shown to carry greater amounts of transient, potentially pathogenic, microorganisms which can increase the rate of udder-infection and concomitant mastitis in the animal. As the potential for and severity of damage resulting from automated milking trauma increases with increased daily milking frequency, the issues of skin condition, microorganism load and ultimately mastitis will be limiting factors for industrial expansion of frequent milking paradigms.

Bovine mastitis is an inflammation of the udder. This condition, which is almost exclusively initiated by pathogenic microorganisms that have entered the teat canal after the milking process, occludes milk flow and production, and can permanently impair an animal's future ability to produce milk. The usual sources of harmful microorganisms include unsanitary milking equipment, the milker, other mastitic animals, an unsanitary stable/pen environment, and the animal's own elimination (defecation/urination) processes. Financial loss due to mastitis have been estimated in the hundreds of millions of dollars in the United States alone. Furthermore, mastitis-related milk losses range from 10–25%.

It is known to perform post-milking teat sanitization with a germicidal agent to decrease mastitis. The post-milking teat decontamination should (1) eradicate most microorganisms on the teat skin, thereby reducing the number which can enter the teat canal and cause infection, and (2) heal minor skin lesions and contribute to the overall health of the udder.

Recently it has been concluded by the U.S. National Mastitis Council that the use of a pre-milking sanitization step further decreases mastitis, and presents other benefits, such as decreasing the surface pathogen load (such as *Escherichia coli* and *Listeria* spp.) and pathogen-related toxin content of milk. Therefore, the industrial recommendation for the use of teat sanitizers presently involves both a pre- and post-milking application. The presently-recommended process of milking is therefore as follows: prior to milking, the teats of the animal to be milked are sanitized with the pre-milking sanitizer, which is then quickly wiped off with a clean towel. The animal is then milked with the automated milker. After milking, the teat is highly susceptible to infection, because the teat-end sphincter muscle (responsible for closing the teat-end) remains open for approximately 30 minutes after milking. Therefore, a post-milking sanitizer is applied and left on the skin (i.e. not rinsed off or deliberately removed) until the next milking.

Because the teat sanitizer is left on the skin for a long period of time, the formulation must not have a tendency to irritate or damage the skin. Any toxic effects would be even more pronounced in a four-times daily milking herd, where the pre- and post-milking sanitization applications could reach up to eight times per day. Due to the difficulty in formulation of a composition which has a satisfactory antimicrobial activity but which also does not damage the skin, the majority of compositions exist in the field which are indicated for use as either a pre-milking, biocidal sanitizer, or as a post-milking biocidal sanitizer/skin conditioner. Generally, the pre-milking sanitizers contain a greater germicidal activity (usually a greater concentration of biocidal active ingredients) than post-milking sanitizers/conditioners because the pre-milking sanitizer does not remain in prolonged contact with the skin.

Active ingredients for teat sanitizer compositions include iodine, stabilized chlorine and quaternary amines, although others have been used. Iodine is perhaps the most widely used active ingredient in such compositions, mainly due to its low cost and fairly broad antimicrobial spectrum. At concentrations allowable in milk, however, iodine has a relatively slow kill time in comparison to other popular active agents, and importantly confers no persistence of antimicrobial activity (i.e. continued killing ability due to retention of the active ingredient in the target tissue) with continued use. Furthermore, at concentrations necessary for usefulness as a biocidal agent, iodine damages the udder skin in frequent milking situations and may not be compatible with other active antimicrobial agents used at other steps in the milking process. Even in once- to twice-daily milking situations, iodine can have a long-term negative effect on the udder skin condition, in part due to tissue denaturation, and to the formation of salts of the counter-ion with environmental anions (e.g. Cl$^-$) on the skin surface after the formulation has dried.

Elemental chlorine is a potent germicidal agent which exerts its antibacterial action in both the elemental form and as undissociated hypochlorous acid (HOCl). The concentration of undissociated HOCl (and therefore the bactericidal activity) of chlorine is pH dependent, with antimicrobial activity falling off sharply in alkaline pH situations. Chlorine is a highly reactive element and can be bound to organic material, which decreases the bactericidal efficacy. Accordingly, in the presence of excessive organic matter, chlorine is not the disinfectant of choice. Chlorine also has a very limited application as an antiseptic agent because of the difficulty of handling the element in the gaseous state and because chlorine/water is very unstable. More useful for disinfection applications are several compounds that slowly yield hypochlorous acid. Such compounds can be regarded as chlorophors, even though the ultimate product is HOCl. The germicidal efficacy of such compounds is related to the case and extent of the liberation of HOCl. In the dairy industry, a number of teat disinfectants make use of chlorine present in the form of hypochlorite. Solutions of hypochlorite are relatively unstable and must therefore be prepared just prior to use. The utility of stabilized chlorine sanitizers is limited in the field because they are binary compositions (i.e. require the addition of an activating solution prior to use), and because they can have an extremely short shelf-life (measured in hours) once activated. Furthermore, these compositions tend to be the most expensive in the industry, in part due to manufacturing and packaging requirements for the base solutions and activators. In addition, stabilized chlorine sanitizers can be inconvenient to the end user from the standpoint of larger space requirements for on-site storage, and susceptibility to misuse (during mixing for activation) by inexperienced dairyhands. From the standpoint of tissue compatibility, chlorophors are not only germicidal, but can dissolve tissue and blood clots, thereby irritating the skin with frequent application and inhibiting clotting. As with iodine and iodophor formulations, elemental chlorine and chlorophors have no residual antimicrobial activity attributable to a build-up of residual active in the skin.

Quaternary amines have been used for several decades as active ingredients in antimicrobial teat washes. Typically, these formulations have been of limited usefulness in the field, because the active ingredient is neutralized by environmental anions. Therefore, by themselves, quaternary amines as active agents for antisepsis in high-soil load conditions, or in the presence of hard water, have limited effectiveness. An example of a teat-wash containing quaternary amines as actives is described by Caughman et al. (U.S. Pat. No. 3,993,777). This composition contains the active ingredient in the presence of an aqueous composition containing nonionic and anionic surfactants, and an emollient (including allantoin). However, the composition suggested by Caughman et al. is of limited utility due to the fact that anions inactivate the cationic active agents. Although ephemeral suspensions of anions and cations may be formulated and can coexist in solution with appropriate nonionic buffers, such formulations are stable only in a narrow range of temperatures, which limits their field utility. Further, the formulations of Caughman et al. form a pliable film barrier about the teat which can actually promote infection. In fact, barrier type teat dips are counterindicated for the skin in teat dip applications, in that barrier adhesion involves bonding (ionic, covalent and/or hydrogen) between applied chemicals and elements (comeocytes, lipids, etcetera) in the upper layers of the stratum comeum. The removal of such barrier products invariably also strips away the layers of cells to which the barrier was anchored. Therefore, continued use and removal of barrier products in a frequent milking paradigm with pre and/or post milking applications can have detrimental erosive effects on sensitive udder and teat skin.

Another method by which the activity of the quaternary amine has been improved in high soil-load environments is through shielding the active in an aqueous composition containing both nonionic and amphoteric surfactants. Such a system, in addition to decreasing the exposure of the active quaternary amine to inactivating elements, such as anions, facilitates the penetration of the active agent into living tissue. The practical application of such a system may be improved in living tissue with the addition of allantoin, a compound which is a cell proliferant, a mild keratinolytic, and which differentially partitions between mammalian and prokaryotic cells. However, compositions derived from this art and applied as teat washes, while performing extremely well as antiseptic compositions, perform only moderately well in maintaining skin condition in low frequency milking, and fail to maintain proper skin condition with high frequency milking.

The known formulations involving an antimicrobial active ingredient delivered to the skin in the context of a delivery system containing allantoin, nonionic, amphoteric and cationic surfactants alone are intended for speed of antimicrobial action with limited product residue at the skin surface; they are not intended for use with high concentrations of skin emollients necessary for satisfactory performance of a teat sanitizer.

In light of the foregoing, there is a need in the industry for antiseptic pre- and post-milking compositions that are highly effective skin decontaminants for the prevention of mastitis but, which at the same time, leave the udder and teat skin in good condition for milking at either low or high frequencies. In addition, such compositions should provide a rapid kill of mastitis-causing microorganisms and be water-soluble, non-toxic and non-sensitizing. The compositions should also possess a measurable degree of persistence of antimicrobial activity with continued use and confer a measure of protection of the active agent therein from inactivation by hard water. The compositions also preferably provide a visual indication (e.g., color) that indicates that the composition has been properly applied. Such compositions would benefit dairies that milk at low frequency, and eliminate one of the major impediments to further practical development of high-frequency milking dairies.

SUMMARY OF THE INVENTION

Formulations of the present invention utilize a protective system of allantoin and nonionic, amphoteric and cationic surfactants in conjunction with a significant emollient system. While not being bound in particular to any specific theory of mechanism of action, it is thought that this system decreases the interaction of ionic microbicides with non-target counterions in the environmental milieu and simultaneously provides long term protection to the delicate tissue of the udder, especially during the occlusive vacuum encountered during the milking process. With the inclusion of such a protective surfactant delivery system, less inactivation of the microbicide occurs, and formulations may achieve similar antimicrobial efficacy with lower overall concentrations of microbicide.

The present aqueous compositions comprise an ingredient, or combination of ingredients, which will effect a rapid kill of mastitis-causing microorganisms. Antimicrobial compositions are set forth which contain a biologically effective, therapeutic, non-toxic quantity of an antimicrobial agent in admixture with either a nonionic, cationic, or amphoteric surfactant, or mixture of such surfactants. The preferred antimicrobial agents are quaternary ammonium compounds, especially benzalkonium chloride, present in an amount of from about 0.0005–0.5 weight percent of the antimicrobial composition. Various other antimicrobial agents can be used in combination with or as a replacement for, the quaternary ammonium compounds.

The antimicrobial compositions preferably also contain a keratolytic agent such as allantoin. As mentioned above, the presence of the allantoin increases the effectiveness of the antimicrobial compositions. The allantoin or other keratolytic agent is present in the antimicrobial compositions in an amount in the range of 0.05–5 weight percent.

The antimicrobial compositions preferably also contain a relatively high weight percent of emollients consisting of a water-soluble refatting agent, and/or glycerine. Such emollient systems are critical to the maintenance of skin health under frequent milking conditions. Although such agents may be chosen from the wide variety of emollients available in the art, preference is given to those of food grade. The emollient system is preferably present in the concentration range of 2.5–20 weight percent of the antimicrobial composition.

DETAILED DESCRIPTION OF THE INVENTION

The present invention provides antimicrobial compositions and methods for their application to animal teat, udder, and mucous membrane tissues. The present invention also provides methods of preparing the antimicrobial compositions. The antimicrobial compositions contain an antimicrobial agent or mixture thereof and a surfactant or mixture thereof. The antimicrobial agent is present in the antimicrobial composition in a biologically effective, therapeutic, non-toxic concentration. Preferably, a keratolytic agent or mixture thereof is present in the compositions. Also preferably, an emollient or emollient system is present in the compositions. Unless explicitly stated otherwise, all weight percentages in the specification and claims are based on the total weight of the antimicrobial composition.

The antimicrobial agents present in the antimicrobial compositions are preferably quaternary ammonium compounds, for example, benzalkonium chloride, benzethonium chloride, methylbenzethonium chloride, and didecyldioctyl ammonium chloride, more preferably benzalkonium chloride. The concentration of the quaternary ammonium compound present in the antimicrobial compositions ranges from about 0.0005 to about 0.5, preferably from about 0.005 to about 0.25, and more preferably from about 0.05 to about 0.13, weight percent. Other antimicrobial agents that may be used in the composition of the present invention, alone or in combination, include other antimicrobial quaternary amines and related compounds, such as, for example, monoalkyltrimethyl ammonium salts, dialkyl ammonium salts, heteroaromatic ammonium salts, polysubstituted quaternary ammonium salts, bis-quaternary ammonium salts and polymeric quaternary ammonium salts.

Still other antimicrobial agents, also referred to as germicidal agents, which may be used in compositions of the present invention alone or in combination, include phenols, including cresols and resorcinols. For example, parachlorometaxylenol is a suitable agent for use in the compositions of the present invention. Several phenol derivatives are more potent than phenol itself, and the most important among these are the halogenated phenols, bis-phenols and resorcinols. Examples of resorcinols useful in compositions of the present invention include resorcinol, hexylresorcinol, hexachlorophene, parabens, thymol, chlorothymol, parachlorometaxylenol, orthophenylphenol, p-tertiary butylphenol, p-tertiaryamylphenol, o-benzylphenyl-p-chlorophenol, p-chlorophenol, camphorated p-chlorophenol, tetrabromomethylphenol, and 2,6-dimethyl-4-chlorophenol. Resorcinols and other phenolic compounds may be present in stated compositions at about 0.0005–1 percent by weight, preferably from about 0.005 to about 0.1 weight percent, and more preferably from about 0.05 to about 0.075 weight percent.

The antimicrobial compositions are prepared with the incorporation of a surfactant that is cationic, nonionic, amphoteric, or a combination thereof. Since benzalkonium chloride is chemically stable within a pH range of about 3 and about 9, when the antimicrobial agent comprises benzalkonium chloride, the surfactant is preferably chemically stable within that pH range. Further, anionic surfactants are not preferred when the antimicrobial agent comprises a quaternary ammonium salt due to their incompatibility with the quaternary ammonium compounds. Various cationic, nonionic, or amphoteric surfactants can be used which are chemically stable in the stated pH range and which are pharmaceutically acceptable and non-toxic. The surfactant, or mixture thereof, is present in an amount of about 0.001 to about 10, preferably about 0.005 to about 5, and more preferably about 0.01 to about 1, weight percent of the antimicrobial composition. Examples of nonionic surfactants include, among others, alkanolamide, alkyl dimethylamine oxide, coconut monoethanolamide, cetyl dimethylamine oxide, stearamine oxide, oleamine oxide, and preferably cocoamidopropyl dimethyl amine oxide. Examples of cationic surfactants include, among others, trimethyl cetyl quaternary ammonium chloride, trimethyl coco quaternary ammonium chloride, diquatemary polydimethylsiloxane, and preferably cetyl trimethyl ammonium chloride. Examples of amphoteric surfactants include, among others, cocoamido betaine, oleyl betaine, cocoamphodiacetate, cocamidopropyl hydroxysultaine, and preferably cocoamidopropyl dimethyl betaine. Individually, it is preferred that the surfactants, if employed, be present in the antimicrobial composition in the following amounts. The amphoteric surfactant can be present in an amount of between about 0.001 and about 10, preferably between about 0.01 and about 6, and more preferably between about 0.02 and about 1 weight percent; the nonionic surfactant can be present in an amount of between about 0.001 and about 7.5, preferably between about 0.005 and about 5, and more preferably between about 0.01 and about 1, weight percent; the cationic surfactant can be present in an amount of from about 0.001 to about 5, preferably about 0.01 to about 2.5, and more preferably about 0.05 to about 1.5, weight percent. When a combination of nonionic and amphoteric surfactants is employed, the concentration ratio of nonionic to amphoteric surfactant is preferably between about 70:30 and about 85:15, and more preferably between about 75:25 and about 80:20. However, concentration ratios of nonionic to amphoteric surfactants of between about 30:70 and about 15:85, and more preferably of between about 25:75 and about 20:80, can be used. The antimicrobial compositions are preferably prepared with the incorporation of a keratolytic agent, such as allantoin (glyoxyldiureide or 5-ureidohydantoin ($C_9H_6N_4O_3$)). Allantoin can be used in its base form, as a metal complex (e.g., aluminum chlorohydroxyallantoinate and aluminum dihydroxyallantoinate), or as an amino acid complex (e.g., allantoin N-acetylmethionate complex). Other keratolytic agents useful in the compositions include triacetin, acetic acid, and salicylic acid, which are all strongly acidic, along with polyoxyethylene lauryl ether and panthenol. Antimicrobial compositions containing benzalkonium chloride are preferably formulated with allantoin since the other keratolytic agents are generally chemically incompatible with the quaternary ammonium compounds. The keratolytic agent is present in the antimicrobial compositions in an amount of about 0.05 to about 5, preferably about 0.25 to about 2.5, and more preferably about 0.5 to about 1, weight percent.

The antimicrobial compositions are preferably prepared with the incorporation of a chemical agent or agents that have an emollient activity on the skin. Anhydrous oil systems and water-in-oil systems are not preferred in the present invention, due to the fact that residual oil can promote adhesion of waste particulate matter and compromise the antimicrobial effectiveness of the composition. Therefore, oil-in-water compositions are preferred in the present compositions. The preferred emollient system for the antimicrobial compositions also includes a water-soluble refatting agent. The preferred emollient for the compositions is glycerol in combination with ethoxylated partial glyceride fatty acid esters, however, the various other emollients that are useful in the present composition include those compatible with the active agent or agents and which promote general skin health and integrity in high frequency milking conditions. These include branched chain esters, ethoxylated partial glyceride fatty acid esters, protein derivatives, lanolin and lanolin derivatives, and fatty alcohol ethoxylates, emollient oils, fatty acids, fatty alcohols and their esters. The relative concentrations of emollient and refatting agents in the composition are easily determined by those skilled in the art. The total concentration of the emollient and re-fatting agents in the antimicrobial compositions is generally about 2.5 to about 20, more preferably about 5 to about 15, and even more preferably about 7.5 to about 10 weight percent.

Other adjuvants, such as pH adjustors, can be blended with the antimicrobial compositions. Useful pH adjustors can be either organic or non-organic acids or bases, alone or in combination with their respective salts. Preferred acidifying agents include, for example, citric acid, sorbic acid, ascorbic acid, malic acid, and succinic acid. Preferred basefying agents include, for example, triethanolamine, ammonium hydroxide, potassium hydroxide, and sodium hydroxide. The pH adjustors, when present, are used in sufficient quantities to bring the pH of the antimicrobial composition into the desired range, generally from about pH 3 to about pH 9. Other adjuvants can include defoamers, such as dimethicone and dicyclomethicone; emollients, such as oleyl alcohol, oleyl lanolate, and lanolin; and moisturizers and humectants, such as vitamin E (alpha tocopherol). In addition, optional ingredients may include both water and oil-soluble vitamins and wound-healing agents (e.g., proteins, lipids, nucleic acids, etcetera). When used, such adjuvants are preferably present in an amount of from about 5,000 to about 15,000 I.U. per ounce of the composition.

The antimicrobial compositions are preferably prepared with a preservative or mixture thereof. Various preservatives are known in the pharmaceutical industry, and the selected preservative is advantageously selected such that it has antimicrobial activity and thus prevents microbial growth. Preferred preservatives include antimicrobial cationic, nonionic or amphoteric surfactants; parabens, such as the methyl and propyl parabens; urea derivatives, such as imidazolidinyl urea and diazolidinyl urea; the cis isomer of 1-(3-chloroallyl)-3,5,7-triaza-1-azonia adamantane chloride (CFTA designation, quaternium-15); and other standard food grade preservatives. The amounts of these preservatives to be blended with the antimicrobial compositions are easily determined by one skilled in the art, however the amount preferably is below about 1.5 weight percent.

The antimicrobial compositions can optionally include stabilizers and thickening agents to achieve viscosities within a useful range appropriate for the mode of application. Such agents include hydroxypropyl methylcellulose, hydroxypropyl cellulose, methyl cellulose, carboxy methylcellulose, emulsifying waxes, alkyl triammonium methosulfate, and ceteraryl octanoate. When used, the total concentration of the stabilizers and thickening agents in the antimicrobial compositions is generally about 0.05 to about 4, more preferably at least about 0.25 to about 2, and even more preferably about 0.3 to about 1.5 weight percent. However, formulations wherein the total concentration of the stabilizers and thickening agents is less than about 0.1 weight percent, and preferably not more than about 0.05 weight percent, can be utilized. Although the compositions are aqueous based, certain ingredients may require the presence of a more lipophilic solvent for proper stabilization. Preferred additional solvents are polyhydric alcohol solvents, or "polyol" solvents, such as the polyalkylene glycols having alkylene moieties containing about 2–3 carbon atoms, preferably the polyethylene glycols. Molecular weight ranges of from about 200–4000 are preferred for the polyalkylene glycols (e.g., propylene glycol). These polyol solvents are useful as humectants and emollients and serve to solubilize the paraben compounds.

The antimicrobial compositions are also preferably prepared with a coloring agent such that the composition is visible to the naked eye on the skin after normal use. Such coloring agents may be drawn from the various certified coloring agents available that are of pharmaceutical grade, and that will not interfere with the antimicrobial or skin protecting properties of the composition. An example includes, but is not limited to FD&C Blue 1, and similar coloring agents. The amounts of these coloring agents are easily determined by one skilled in the art; however, the amount is preferably below about 6.0 weight percent of the composition.

The balance of the composition is an aqueous solvent, preferably freshly distilled water. Preferably the solvent for the system is freshly distilled water. Deionized water is not preferred as the deionizing resins can result in the presence of pathogens in the deionized water. Further, salts possibly present in deionized water can deactivate quaternary ammonium compounds. The amount of water in the compositions is generally at least about 60, preferably at least about 70, more preferably at least about 80, and even more preferably at least about 85, weight percent.

Although various formulations can be prepared for the stated multiple end uses, preferred ranges for various components used in an antimicrobial composition for eradication of fungal, bacterial and viral topical infectious agents of mammalian udders, teats and adjacent tissue, especially for treatment and prevention of mastitis, are set forth in Table 1.

TABLE 1

| Component | Broad | Intermediate | Preferred |
| --- | --- | --- | --- |
| benzalkonium chloride | 0.0005–1.0 | 0.005–0.5 | 0.05–0.13 |
| glyoxyldiureide | 0.05–5.0 | 0.25–2.5 | 0.5–1.0 |
| propylene glycol | 0.00–15.0 | 0.25–12.0 | 0.5–8.0 |
| hydroxypropyl methylcellulose | 0.00–4.0 | 0.25–2.0 | 0.5–1.5 |
| cocoamidopropyl dimethyl betaine | 0.001–8.0 | 0.01–6.0 | 0.02–1.0 |
| cocoamidopropyl dimethyl amine oxide | 0.001–8.0 | 0.005–5.0 | 0.01–1.0 |
| cetyl trimethyl ammonium chloride | 0.001–5.0 | 0.01–2.5 | 0.05–1.0 |
| methyl paraben | 0.001–1.0 | 0.02–0.8 | 0.05–0.25 |
| propyl paraben | 0.001–1.0 | 0.02–0.8 | 0.05–0.25 |
| cis isomer of 1-(3-chloroallyl)-3,5,7-triaza-1-azoniaadamantane chloride | 0.01–1.0 | 0.05–0.5 | 0.1–0.25 |
| diazolidinyl urea | 0.001–1.0 | 0.05–0.5 | 0.1–0.25 |
| triethanolamine | trace | trace | trace |
| citric acid | trace | trace | trace |
| Emollient | 2.5–20.0 | 5.0–15.0 | 7.5–10.0 |

TABLE 1-continued

| Component | Broad | Intermediate | Preferred |
|---|---|---|---|
| Coloring agent | 0.5–6.0 | 1–5 | 2–3 |

The antimicrobial compositions are generally prepared by blending the constituents together until a homogeneous mixture results. If surface treated hydroxypropyl methyl cellulose is used as a stabilizer, the hydroxypropyl methyl cellulose is preferably blended at the beginning of the preparation in the aqueous solution with the pH of the solution being preferably adjusted to about 8–10 to aid in the dissolution. If nonsurface treated hydropropyl methyl cellulose is used, such as with mouthwash compositions, the temperature of the mixture is preferably adjusted upward during the addition until the stabilizer is dissolved. A preferred process for preparing an antimicrobial composition of the present invention, such as those set forth in Table 1 and useful for the prevention and treatment of mastitis, is to dissolve the cis-isomer of 1-(3-chloroallyl)-3,5,7-triaza-1-azoniaadamantane chloride (Dowicill 200, Dow Chemical Co.) into distilled water. Small amounts of hydroxypropyl methyl cellulose are then added and dispersed into the medium. A solution of triethanolamine is then added dropwise to the stirred solution to adjust the pH to about 8–10 to allow the stabilizer to dissolve. An aqueous solution of citric acid is then used to lower the pH below about 7, preferably to about 4.5–6.5. Next, the cocoamidopropyl dimethyl betaine, cocoamidopropyl dimethyl amine oxide, and cetyl trimethyl ammonium chloride are added using mild agitation. The pH is then adjusted to about 6–6.5 by the dropwise addition of the acidic or basic solutions. The benzalkonium chloride is added with stirring while maintaining the pH at about 6–6.5. The preservatives, the parabens, diazolinoyl urea, and propylene glycol are then added (such as a mixture of the preservatives with propylene glycol sold as Germben II-E, Sutton Laboratories) and mixing is continued until the parabens are dissolved yielding a clear colorless solution. Next, the allantoin is added and dissolved to yield a clear colorless solution having a pH of about 6–6.5. Next, the emollients are added, followed by the coloring agents. The final solution should have a pH of about 6–6.5.

The antimicrobial compositions can be used for various applications with the application route and dosage regimen are dictated by the frequency of milking and/or the skin condition of the animal. As an example of possible applications of the invention, the compositions can be used in mammals as a pre- and post-milking application to decrease the potential for mastitis, and/or subcutaneous dermatological pathologies stemming from microbial infections. An example of this includes administering the compositions to mammalian skin, specifically the udder and teats of milking animals. The composition can be applied as a cleanser, scrub (cleanser with abrasive properties), lotion, or gel. The compositions can also be used in a therapeutic manner. For example, the compositions can be used in both a cleanser or a scrub composition to help heal udder and teat skin which has been damaged by frequent milking. Additional applications for the sanitizer include vaginal cleansers, calving sanitizers, burn disinfectants, wound healing aids, and perianal and colostomy wipe applications. For wipes, the formulation of the present invention may be applied to paper or cloth towelettes.

Additional objects, advantages, and novel features of the present invention will become apparent to those skilled in the art upon examination of the following examples.

EXAMPLES

Example 1

A composition in accordance with the present invention having the following composition (Solution 1) was prepared according to the method of preparation described above for field evaluation of in vivo performance.

| Solution 1 | |
|---|---|
| COMPONENT | WEIGHT PERCENT |
| Water (dd) | 90.530 |
| Triethanolamine (99%) | — |
| Hydroxypropylmethyl cellulose | 0.250 |
| Citric Acid | — |
| Cocmaidopropyl dimethyl betaine (31%) | 0.020 |
| Carsoquat CT-429 (29%) | 0.073 |
| Cocamidopropylamine oxide (31%) | 0.010 |
| Quaternium 12 (50%) | 0.100 |
| Benzalkonium chloride (50%) | 0.033 |
| Glycerin | 4.985 |
| Polyethylene glycol-glycerides adduct | 2.000 |
| Glyoxydiureide | 0.500 |
| Cineole/eucalyptol | 0.11 |
| FD&C Blue 1 | 0.010 |

For comparison purposes a composition having the following composition (Solution 2) was also prepared according to the method of preparation described above.

| Solution 2 | |
|---|---|
| COMPONENT | WEIGHT PERCENT |
| Water (dd) | 80.695 |
| Triethanolamine (99%) | — |
| Hydroxypropylmethyl cellulose | 0.250 |
| Citric Acid | — |
| Cocamidopropyldimethyl amine oxide (31%) | 0.620 |
| Cetyltrimethyl ammonium chloride (29%) | 0.290 |
| Cocmaidopropyl dimethyl betaine (31%) | 0.310 |
| Quaternium 12 | 0.400 |
| Benzalkonium chloride (50%) | 0.130 |
| Glyoxydiureide | 0.500 |
| Cineole/eucalyptol | 0.110 |
| FD&C Blue 1 | 0.010 |

A commercially available iodine-based teat wash solution containing iodine complexed with polyvinyl-pyrrolidone (Povidone Iodine (1.0% freely available iodine; Teatkote® Sanitizing Teat Dip, Westfalia-Surge, Inc.)) was also tested for comparison purposes.

The testing was performed as follows. Ten milking cows per group were placed on a twice daily milking regimen with pre- and post-milking decontamination using a spray-application device (approximately 2 ml solution per application). The antimicrobial compositions applied prior to milking were removed by wiping the teats with a clean disposable towelette before the animal was milked; the antimicrobial compositions applied immediately after the milking were left on the animal and not rinsed off. The skin condition of the teat quarters was assessed after 14 days of treatment, and was judged on a 1–5 scale, with 1 representing an excellent skin condition and 5 representing a poor skin condition. The following results were obtained:

| Treatment Group | Starting Condition | Final Condition |
|---|---|---|
| Solution 1 | 3.5 ± 0.3 | 1.0 ± 0.0 |
| Solution 2 | 3.5 ± 0.5 | 4.7 ± 0.3 |
| Iodine Solution | 3.4 ± 0.6 | 2.8 ± 0.2 |

As seen from the above results, Solution 1 provided improved skin condition as compared to either Solution 2 or the iodine-based teat wash.

Example 2

The antimicrobial activity of Solution 1 and the iodine-based teat wash of Example 1 were tested as follows. Twenty-five milking cows per group on a 4-times-daily milking regimen were treated pre- and post-milking with either Solution 1 or the iodine-based teat wash for 6 weeks. The skin condition of the treated teat quarters was assessed after 14 days of treatment, and was judged on a 1–5 scale, with 1 representing an excellent skin condition and 5 representing a poor skin condition. In addition, somatic cell counts and cases of clinical mastitis were monitored by standard veterinary methodology at the end of the test period for both test groups. The results were as follows:

| | Skin Condition | | Mastitis | | Somatic Cell Count | |
|---|---|---|---|---|---|---|
| | Start | Finish | Start | Finish | Start | Finish |
| Iodine solution | 3.8 ± 0.4 | 4.2 ± 0.3 | 11% | 11% | $8.71 \times 10^5$/ml | $2.5 \times 10^6$/ml |
| Solution 1 | 3.8 ± 0.3 | 1.0 ± 0.0 | 11% | 7.4% | $3.3 \times 10^6$/ml | $7.1 \times 10^5$/ml |

These results demonstrate that the teat skin condition of animals treated with Solution 1 improved, while the skin condition of animals receiving the iodine solution appeared to have at best remained at the same mediochre quality score. The incidence of clinical mastitis reported for the Solution 1 group was approximately 49% less than that of the iodine solution-treated group. Likewise, although the mean somatic cell count (white blood count) in the Solution 1 group at the beginning of the test period was approximately 3.8 fold greater than the control iodine solution group, it fell to 3.5 fold less than the control group by the end of the test.

Example 3

The reduction of topical bacteria on teats using Solution 1, the iodine-based teat wash of Example 1, and a solution containing hypochlorous acid (activator: 2.64% Lactic Acid, 10% Glycerin; base: 0.64% Sodium Chlorite; 4XLA; Alcide Corporation) was assessed as follows: bacteria counts application on the quarters of 3–4 milking cows per group pre and post product were obtained by swabbing quarters with sterile swabs, and submerging swabs in 2 ml of nutrient broth containing appropriate neutralizers for no longer than 60 minutes. Aerobic plate counts (APC) of swab solutions were carried out by plating 15 μl of the swab sample on nutrient agar, and allowing colonies to develop for 48 hours at 37° C. In addition, to assay for the presence of Group B streptococci on the teat skin, samples were grown on blood agar plates in proximity to a *Staphylococcus aureus* test strain (CAMP test). Following the initial swabbing for baseline counts, teat quarters were dipped in the antimicrobial composition of interest and wiped down after 10 seconds with a sterile cotton towel. Bacteria remaining on the teat surface were then sampled by swabbing as described above. The bacterial reduction results were as follows.

| | Log Bacteria Reduction | | |
|---|---|---|---|
| | Solution 1 | Iodine-based teat wash | Hypochlorous Acid |
| APC Test | 2.46 ± 0.51 | 2.24 ± 0.29 | 2.10 ± 0.36 |
| CAMP Test | 2.48 ± 0.35 | 1.78 ± 0.33 | 2.29 ± 0.22 |

The data displayed represent the mean ±SD (standard deviation) of 12–16 samples. These results indicate that the antimicrobial composition of the present invention is at least as effective in reducing the aerobic flora present on the teat skin, including Group B streptococci, as the other, commercially available teat sanitizing compositions.

Example 4

In vitro time-kill assessment of the antimicrobial performance of an antimicrobial composition in accordance with the present invention having the following composition (Solution 3) was performed using standard methodology (NCCLS Document M7-A3: Methods for dilution antimicrobial susceptibility tests for bacteria that grow aerobically-third edition; Approved standard) using *Escherichia. coli* (ATCC 11229). For comparison purposes, a negative control comprising Solution 4 was also assessed as described above.

| | Solution 3 |
|---|---|
| COMPONENT | WEIGHT PERCENT |
| Water (dd) | 97.7 |
| Triethanolamine (99%) | qs |
| Hydroxypropylmethyl cellulose | 0.250 |
| Citric Acid | qs |
| Cocamidopropyl betaine (31%) | 0.620 |
| Cocamidopropyl dimethyl amine oxide (31%) | 0.310 |
| Cetyltrimethylammonium chloride (50%) | 0.400 |
| Parachlorometaxylenol (50%) | 0.100 |
| Glyoxydiureide | 0.500 |
| Cineole/eucalyptol | 0.110 |
| FD&C Blue 1 | 0.010 |

| Solution 4 | |
| --- | --- |
| COMPONENT | WEIGHT PERCENT |
| Water (dd) | 97.8 |
| Triethanolamine (99%) | qs |
| Hydroxypropylmethyl cellulose | 0.250 |
| Citric Acid | qs- |
| Cocamidopropyl betaine (31%) | 0.620 |
| Cocamidopropyl dimethyl amine oxide (31%) | 0.310 |
| Cetyltrimethylammonium chloride (50%) | 0.400 |
| Glyoxydiureide | 0.500 |
| Cineole/eucalyptol | 0.110 |
| FD&C Blue 1 | 0.010 |

The averaged results from the three trials performed are as follows:

| Condition | % Reduction 15 sec Exposure Time | % Reduction 30 sec Exposure Time |
| --- | --- | --- |
| Negative Control | 0.00 | 0.00 |
| Solution 3 | =99.999 | =99.999 |

The above results clearly indicate that Solution 3 provides excellent in vitro antimicrobial performance.

What is claimed is:

1. An antimicrobial composition comprising:
   from about 0.0005 to about 1 weight percent of an antimicrobial agent;
   from about 0.05 to about 5 weight percent of a keratolytic agent;
   from about 0.001 to about 10 weight percent of a surfactant;
   at least about 60 weight percent water; and
   from about 2.5 to about 20 weight percent of an emollient.

2. The composition of claim 1 wherein the antimicrobial agent comprises at least one quaternary ammonium compound.

3. The composition of claim 2 wherein the antimicrobial agent further comprises a compound selected from the group consisting of antimicrobial phenols and antimicrobial phenol derivatives.

4. The composition of claim 2 wherein the quaternary ammonium compound comprises benzalkonium chloride.

5. The composition of claim 4 comprising between about 0.005 and about 0.5 weight percent benzalkonium chloride.

6. The composition of claim 5 comprising between about 0.25 and about 2.5 weight percent allantoin.

7. The composition of claim 5 further comprising not more than about 15 weight percent propylene glycol.

8. The composition of claim 1 wherein the keratolytic agent is allantoin.

9. The composition of claim 1 wherein the surfactant comprises at least one compound selected from the group consisting of nonionic surfactants, cationic surfactants, amphoteric surfactants, and combinations thereof.

10. The composition of claim 9 wherein the surfactant comprises between about 0.001 and about 8 weight percent of a nonionic surfactant.

11. The composition of claim 9 wherein the surfactant comprises between about 0.001 and about 5 weight percent of a cationic surfactant.

12. The composition of claim 9 wherein the surfactant comprises between about 0.001 and about 8 weight percent of an amphoteric surfactant.

13. The composition of claim 6 wherein the surfactant comprises between about 0.001 and about 8 weight percent of an amphoteric surfactant and between about 0.001 and about 5 weight percent of a cationic surfactant.

14. The composition of claim 13 wherein the surfactant further comprises between about 0.001 and about 8 weight percent of a nonionic surfactant.

15. The composition of claim 1 comprising at least about 80 weight percent water.

16. The composition of claim 15 comprising at least about 85 weight percent water.

17. The composition of claim 1 wherein the emollient comprises a compound selected from the group consisting of water-soluble refatting agents and glycerin.

18. The composition of claim 1 further comprising between about 0.5 and about 6.0 of a coloring agent.

19. The composition of claim 1 further comprising between about 0.01 and about 0.5 weight percent of a preservative.

20. The composition of claim 19 wherein the preservative comprises a compound selected from the group consisting of antimicrobial cationic, nonionic or amphoteric surfactants; urea derivatives; and parabens.

21. The composition of claim 1 further comprising between about 0.25 and about 15 weight percent propylene glycol.

22. The composition of claim 1 the composition is in the form of a cleanser, a scrub, a vaginal douche, a perianal wipe, a colostomy wipe, a calving sanitizer, or a gel.

23. An antimicrobial composition comprising:
   from about 0.005 to about 0.5 weight percent of at least one quaternary ammonium compound comprising benalkonium chloride;
   from about 0.05 to about 5 weight percent allantoin;
   from about 0.001 to about 10 weight percent of a surfactant comprising at least one nonionic surfactant, cationic surfactant, or amphoteric surfactant;
   from about 0.01 to about 0.5 weight percent of a preservative;
   at least about 80 weight percent water; and
   from about 2.5 to about 20 weight percent of an emollient comprising a water soluble refatting agent and glycerin.

24. The composition of claim 23 comprising at least about 85 weight percent water.

25. The composition of claim 24 comprising between about 0.05 and about 0.13 benzalkonium chloride.

26. A composition for the prevention of bovine mastitis comprising:
   from about 0.0005 to about 1 weight percent of an antimicrobial agent;
   from about 0.05 to about 5 weight percent of a keratolytic agent;
   from about 0.001 to about 10 weight percent of a surfactant; and
   at least about 60 weight percent water; and
   from about 2.5 to about 20 weight percent of an emollient;
   wherein the composition effectively reduces susceptibility to bovine mastitis when used daily to treat the udder and teats of a mammal.

27. The composition of claim 26, wherein the composition comprises an effective amount of an emollient to condition the udder and teats of a cow for high frequency milking.

28. The composition of claim 26, wherein treatment of a cow's udder and teat with the antimicrobial composition decreases the incidence of clinical mastitis by about 49% compared to treatment with iodine based solutions.

29. The composition of claim 26, wherein treatment of a cow's udder and teat with the antimicobial composition reduces the mean somatic cell count of the cow's udder and teat at least 3.5 times less than the mean somatic cell count present prior to treatment with the antimicrobial composition.

30. The composition of claim 1 wherein the emollient comprises water soluble refatting agent, glycerin, branched chain esters, ethoxylated partial glyceride fatty acid esters, protein derivatives, lanolin and lanolin derivatives, and fatty alcohol ethoxylates, emollient oils, fatty acids, and esters of fatty alcohols, or combinations thereof.

* * * * *